US012737898B2

(12) United States Patent
Yu et al.

(10) Patent No.: US 12,737,898 B2
(45) Date of Patent: Sep. 15, 2026

(54) RESPIRATION FEATURE EXTRACTION METHOD BASED ON BODY SURFACE SIGNIFICANCE ANALYSIS

(71) Applicant: SOOCHOW UNIVERSITY, Suzhou (CN)

(72) Inventors: Shumei Yu, Suzhou (CN); Yao Yao, Suzhou (CN); Rongchuan Sun, Suzhou (CN); Lining Sun, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 139 days.

(21) Appl. No.: 18/280,914

(22) PCT Filed: Oct. 26, 2022

(86) PCT No.: PCT/CN2022/127637
§ 371 (c)(1),
(2) Date: Sep. 7, 2023

(87) PCT Pub. No.: WO2024/055386
PCT Pub. Date: Mar. 21, 2024

(65) Prior Publication Data

US 2025/0037288 A1 Jan. 30, 2025

(30) Foreign Application Priority Data

Sep. 14, 2022 (CN) .......................... 202211114226.5

(51) Int. Cl.
*G06T 7/246* (2017.01)
*G06T 5/70* (2024.01)
(Continued)

(52) U.S. Cl.
CPC ................ *G06T 7/251* (2017.01); *G06T 5/70* (2024.01); *G06T 7/0014* (2013.01); *G06T 7/12* (2017.01);
(Continued)

(58) Field of Classification Search
CPC ........... G06T 7/251; G06T 7/136; G06T 7/12; G06T 7/337; G06T 7/35; G06T 5/70;
(Continued)

(56) References Cited

U.S. PATENT DOCUMENTS

2012/0226152 A1 9/2012 Porikli

FOREIGN PATENT DOCUMENTS

CN 109727672 A 5/2019
CN 110752004 A 2/2020
(Continued)

OTHER PUBLICATIONS

Yu, Shumei, et al. "Correlated skin surface and tumor motion modeling for treatment planning in robotic radiosurgery." Frontiers in Neurorobotics 14 (2020): 582385. (Year: 2020).*
(Continued)

*Primary Examiner* — Yu Chen
(74) *Attorney, Agent, or Firm* — SZDC Law PC

(57) ABSTRACT

The present application provides a respiration feature extraction method based on body surface significance analysis, including: establishing a body surface voxel model of chest and abdomen respiration motion, which includes acquisition of point cloud information, generation of the voxel model and extraction of respiration motion features; establishing a significance evaluation function by performing significance analysis on different regions of a body surface, and selecting the body surface region with high correlation with tumor motion based on the evaluation function; and performing voxelization on the body surface region, and obtaining effective one-dimensional characterization information of the body surface region using a local linear embedding dimension reduction algorithm. Compared with the prior art, the method avoids an influence of body-surface redundant motion information on precision of the association model,
(Continued)

and compared with a PCC method, the method can avoid harm to the human body caused by continuous irradiation of X rays.

9 Claims, 6 Drawing Sheets

(51) Int. Cl.

| | |
|---|---|
| ***G06T 7/00*** | (2017.01) |
| ***G06T 7/12*** | (2017.01) |
| ***G06T 7/136*** | (2017.01) |
| ***G06T 7/33*** | (2017.01) |
| ***G06T 7/35*** | (2017.01) |
| ***G06T 15/08*** | (2011.01) |
| ***G06T 17/00*** | (2006.01) |
| ***G16H 20/40*** | (2018.01) |

(52) U.S. Cl.

CPC .............. *G06T 7/136* (2017.01); *G06T 7/337* (2017.01); *G06T 7/35* (2017.01); *G06T 15/08* (2013.01); *G06T 17/00* (2013.01); *G16H 20/40* (2018.01); *G06T 2207/10024* (2013.01); *G06T 2207/10028* (2013.01); *G06T 2207/20021* (2013.01); *G06T 2207/30096* (2013.01); *G06T 2210/12* (2013.01); *G06T 2210/41* (2013.01); *G06T 2210/56* (2013.01)

(58) Field of Classification Search

CPC ....... G06T 7/0014; G06T 15/08; G06T 17/00; G06T 2207/10024; G06T 2207/10028; G06T 2207/20021; G06T 2207/30096; G06T 2210/12; G06T 2210/41; G06T 2210/56; G16H 20/40

See application file for complete search history.

(56) References Cited

FOREIGN PATENT DOCUMENTS

| | | |
|---|---|---|
| CN | 114927215 A | 8/2022 |
| CN | 115187608 A | 10/2022 |

OTHER PUBLICATIONS

Wang, Jiateng, et al. "An improved correlation model for respiration tracking in robotic radiosurgery using essential skin surface motion." IEEE Robotics and Automation Letters 6.4 (2021): 7885-7892. (Year: 2021).*

Yu, Shumei, et al. "Characteristics Study on Respiratory Movement of Chest and Abdominal Surface Area for Respiration Tracking in Radiosurgical Robots." 2021 IEEE 11th Annual International Conference on CYBER Technology in Automation, Control, and Intelligent Systems (CYBER). IEEE, 2021. (Year: 2021).*

Wijenayake, Udaya, and Soon-Yong Park. "Real-time external respiratory motion measuring technique using an RGB-D camera and principal component analysis." Sensors 17.8 (2017): 1840. (Year: 2017).*

* cited by examiner

RESPIRATION FEATURE EXTRACTION METHOD BASED ON BODY SURFACE SIGNIFICANCE ANALYSIS

This application is the National Stage Application of PCT/CN2022/127637, filed on Oct. 26, 2022, which claims priority to Chinese Patent Application No. 202211114226.5, filed on Sep. 14, 2022, which is incorporated by reference for all purposes as if fully set forth herein.

FIELD OF THE DISCLOSURE

The present application relates to the field of medical data processing technologies, and particularly to a respiration feature extraction method based on body surface significance analysis.

BACKGROUND OF THE DISCLOSURE

Radiotherapy becomes a mainstream clinical treatment method for tumors, and about 50% of cancer patients require a radiotherapy technology during treatment. A lung cancer is a relatively common malignant tumor, death cases caused by the lung cancer account for almost one third of all cancer death cases, and among all lung cancer patients, non-small cell lung cancer (NSCLC) patients account for up to 80% or more, and early symptoms are not apparent and thus difficult to detect. For a locally advanced NSCLC which is inoperable, stereotactic radiotherapy (SBRT) remains an effective treatment means. SBRT becomes a mainstream treatment scheme for the NSCLC due to its characteristics of a good treatment effect, little pain suffered by patients, a small postoperative recurrence rate, or the like. The radiotherapy technology has evolved from traditional irradiation treatment to a highly conformal technology, and reduces additional damage to normal tissue while increasing an effective irradiation dose. However, due to position particularity of the lung tumor, the lung tumor may perform quasi-periodic motion with a large amplitude along with respiration, and in an initial treatment scheme of the SBRT, methods of abdominal compression, breath holding, gating, or the like, are introduced to reduce an influence of the tumor motion on treatment precision. However, in the methods, comfort of the patient in a treatment process is sacrificed, a real-time respiration tracking system is introduced in a cyber knife, and a tumor position is positioned by establishing an association model of motion of a body surface marking point and motion of the tumor, such that the pain of the patient in the treatment process is greatly reduced while the treatment precision is guaranteed.

In order to establish the association model of body surface characterization information and the tumor motion, researchers study how to extract effective body surface features for many years, and establish the association model of extracted surface feature information and the tumor motion to obtain motion information of the tumor. Someone uses a laser device connected to a treatment couch and orthogonal to a skin surface of the patient. A motion change of one point on a surface of the abdomen is monitored by measuring a relative position of a reflected laser, and linearly fitted with the tumor motion, and an experimental result shows that information acquired by the single marking point is limited and is not enough to characterize the respiration motion of the body surface. In the cyber-knife respiration tracking system, three marking points placed on a surface of the chest of a human body are taken as substitutes of body surface respiration motion, and the tumor position is predicted by establishing a polynomial model of the marking points and the tumor motion; however, tumor positioning precision is greatly influenced by placing positions of the marking points. Someone places 19 infrared LED marking points on a surface of the abdomen of a pig dead for a few minutes, and places four gold marks at the liver in the pig to obtain motion information of the liver, and establishes a body-surface and in-vivo motion association model using a ε-support vector regression method, and a conclusion that more detailed body surface motion information can be obtained using more LED marking point information is obtained by differently combining many of the 19 marking points.

Besides the method in which the marking point is placed on the body surface, researchers also explore non-contact methods for measurement to obtain more comprehensive body surface information. In contrast to the method in which the marking point is required to contact the patient, the non-contact measurement method does not interfere with free respiration of the patient. Someone places a multi-slit light projector and a CCD camera directly above a subject to form a fiber grating vision sensor, and respiration of the subject is monitored by near-infrared multi-slit light projection. However, projection coverage ranges on the chest wall are different due to motion of the patient, such that accurate body surface motion information cannot be measured. Someone designs a structured light system which provides a precise three-dimensional topological structure of a surface of the chest wall, and information characterizing body surface respiration motion is obtained by evaluating a change of a three-dimensional surface of the chest wall in an anatomically consistent measurement region during respiration; however, portability of this method is too poor. Someone uses a depth sensor in conjunction with a non-rigid registration algorithm to monitor deformation of the chest wall. With a technological development of commercial R-GBD sensors, cameras are applied to the field of three-dimensional image information processing by more and more researchers. Someone captures an image of the entire chest and abdomen region with a camera, decomposes data by principal component analysis (PCA) to create a respiration motion model, and acquires body surface respiration motion by reconstructing the image, but reconstruction precision is low. Someone uses a depth camera to track graphs of 11 circular marking points attached to a skintight jacket of a subject, and experiments prove that color and depth information collected by the camera can be used for tracking motion of marks of the chest and the abdomen of the human body in real time.

In previous work, an association model of one-dimensional chest and abdomen body surface feature information and the tumor motion is established based on a chest and abdomen voxel model. One-dimensional feature information capable of characterizing body surface respiration motion is obtained by reconstructing the chest and abdomen body surface voxel model and performing dimension reduction on a voxel dataset of the whole body surface. However, experimental research shows that if all chest and abdomen body surface regions are used as effective regions for respiration motion feature extraction, regions with low correlation with the tumor motion affect accurate expression of respiration motion features in a final result. For example, motion of an edge part of the chest and abdomen body surface and a region below the waist has lower correlation with the tumor motion than motion of the chest and abdomen region. Thus, the present application provides a method for selecting a body-surface significant region, including: dividing a body surface into a plurality of regions with the same size, extracting feature information of each region, calculating correlation between each region and tumor motion, and selecting a high correlation region as the significant region. Finally, an association model of dimension reduction information of the significant region as body surface respiration motion features and the tumor motion is established. However, in this method, tumor motion information is required to be obtained in advance when the significant region is selected, and during radiotherapy of the tumor patient, continuous position information of the tumor cannot be obtained in real time, and therefore, it is necessary to find a method to obtain distribution of the significant region under a condition that the tumor motion is unknown.

SUMMARY OF THE DISCLOSURE

In view of this, an object of the present application is to provide a respiration feature extraction method based on body surface significance analysis, which can specifically solve the existing problems. In order to achieve the object, in the present application, a significance evaluation function is provided to be used for selecting a body surface significant region, and after a body surface is divided into a plurality of regions with the same size and feature information of each region is extracted, the significance evaluation function is constructed by extracting a plurality of indexes capable of characterizing significance of the regions in the feature information to obtain a significance value of each region, a high correlation region is selected as the significant region, and finally, validity of the method is verified through a Bland-Altman consistency check and associated experiments.

A respiration feature extraction method based on body surface significance analysis, comprising:

- establishing a body surface voxel model of chest and abdomen respiration motion, which comprises acquisition of point cloud information, generation of the voxel model and extraction of respiration motion features;
- establishing a significance evaluation function by performing significance analysis on different regions of a body surface, and selecting the body surface region with high correlation with tumor motion based on the evaluation function; and
- performing voxelization on the body surface region, and obtaining effective one-dimensional characterization information of the body surface region using a local linear embedding dimension reduction algorithm.

Generally, the present application has the following advantages and user experiences. The method can effectively extract body surface region information with a high characterization capability during the human respiration motion, and compared with the prior art, the method avoids an influence of body-surface redundant motion information on precision of the association model, and compared with a PCC method, the method according to the present application can select the body-surface effective region under a condition of unknown tumor motion information, can realize real-time update of the body-surface effective region during actual radiotherapy, and avoids harm to the human body caused by continuous irradiation of X rays. The body surface motion information can be acquired more accurately by extracting the features of the body-surface effective region, thus facilitating establishment of a more accurate body-surface-in-vivo motion information association model, and providing more accurate treatment precision for a radiotherapy robot. In future research, a more accurate evaluation function is established in conjunction with different respiration modes of the human body to adapt to a condition that the respiration modes change.

BRIEF DESCRIPTION OF DRAWINGS

FIG. 9 is a diagram of an association effect of an LED marking point, whole body surface region dimension reduction and effective body surface region dimension reduction.

DETAILED DESCRIPTION OF PREFERRED EMBODIMENTS

The present application will be described in further detail with reference to the drawings and embodiments.

1 Chest and Abdomen Respiration Motion Voxel Model

Body surface point cloud information is collected by two Kinectv2 depth cameras, subjected to point cloud processing, and inserted into Octomap to obtain a voxel model. Finally, a dimension of the obtained voxel model is reduced to one-dimensional body surface motion information characterizing body surface respiration motion features using a Locally Linear Embedding (LLE) algorithm. The whole flow is shown in FIG. 1.

1.1 Point Cloud Information Acquisition and Processing

Figure 1:
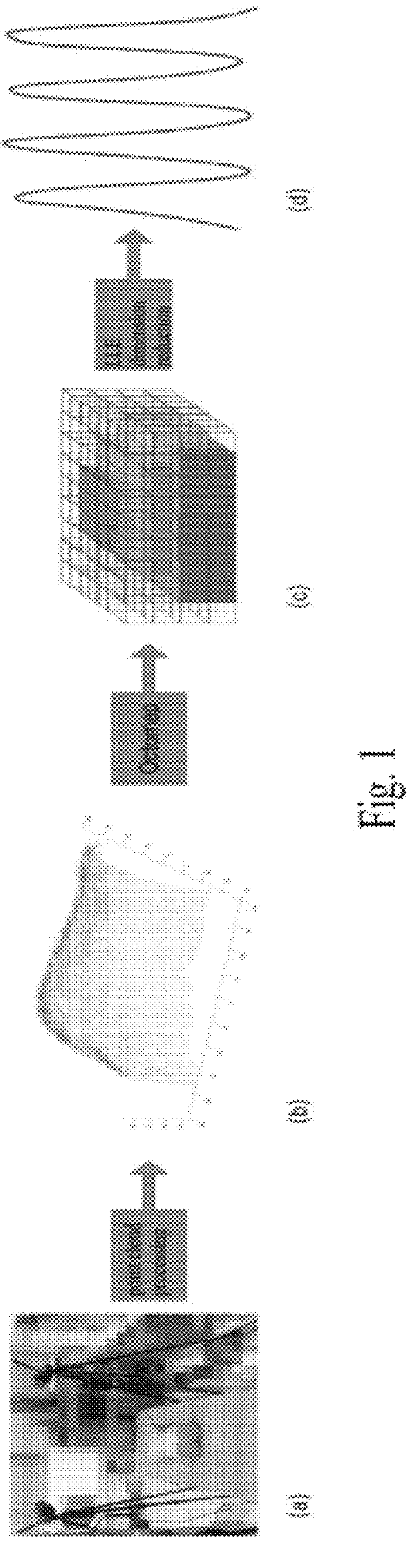
FIG. 1 shows a flow chart of one-dimensional characterization information acquisition based on a voxel model according to the present application.

Since a visual angle of a single depth camera is limited, a collected point cloud has incomplete information, but an excessive number of cameras are prone to generate infrared signal interference, and therefore, two RGB-D depth cameras with fixed positions are selected to collect the point cloud information of a chest and abdomen body surface, and arrangement positions are shown in FIG. 1(*a*). Coordinates of the two cameras are unified to the same coordinate system by using a calibration plate before the point cloud information is collected, noise points are then removed by using a statistical filtering algorithm, two groups of point cloud information are registered by using an Iterative Closest Point (ICP) algorithm, redundant information is then removed by using RGB and boundary threshold segmentation, and finally, point cloud data is smoothened by using a mobile least square algorithm. The processed point cloud information obtained finally is shown in FIG. 1(*b*).

1.2 Voxel Model

After the above point cloud acquisition and point cloud processing work, the smooth point cloud information of the complete chest and abdomen body surface is obtained, the point cloud information is unsystematic and disordered and cannot be subjected to feature extraction, and therefore, the processed point cloud information is inserted into Octomap, and a voxel map is created by defining occupied and idle states of the point cloud in a space. FIG. 1(*c*) shows a chest and abdomen body surface voxel model.

1.3 Body Surface Respiration Motion Feature Extraction

Figure 2:
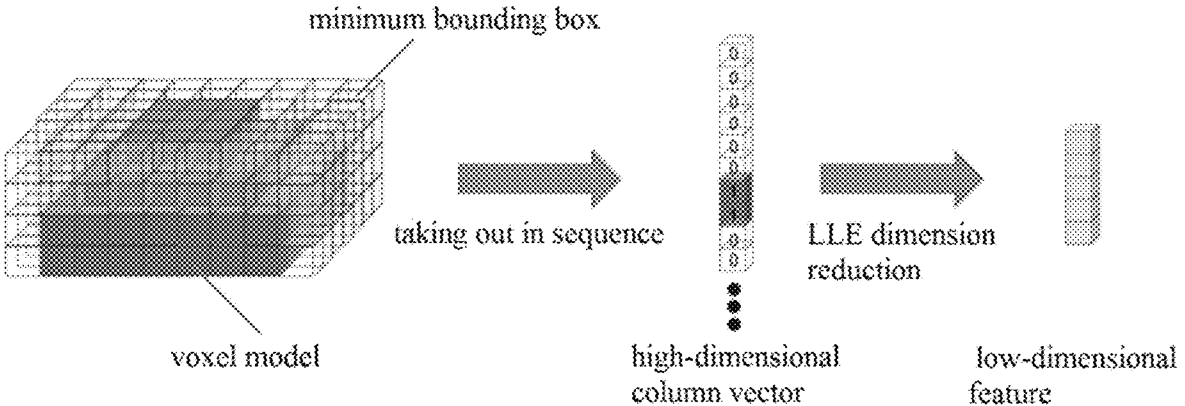
FIG. 2 shows a flow chart of a single-frame voxel model dimension reduction process according to an embodiment of the present application.

Body surface information of each frame is modeled into a voxel model, and the voxel model represents a body surface respiration motion state at one moment. Since the body surface point cloud information has a large amount, the established voxel model is still a high-dimensional feature. In order to reduce dimensions of body surface features, firstly, the voxel models of all frames are traversed, and a rectangular parallelepiped bounding box, i.e., a minimum bounding box, is constructed and can just accommodate the largest one-frame voxel model. Then, voxel blocks are taken from the bounding box according to the same traversal order for each voxel model, so as to form a super-high-dimensional one-dimensional column vector, and finally, the column vector is subjected to dimension reduction to low-dimensional features capable of characterizing the body surface respiration motion features using an LLE algorithm, as shown in FIG. 1(*d*). The LLE dimension reduction process of the single-frame voxel model is shown in FIG. 2.

2 Feature Extraction of Effective Region 2.1 Definition of Effective Region

Selection of the effective region requires simultaneous acquisition of the body surface and tumor motion information, and a specific flow is as follows: 1) uniformly dividing the body surface into a plurality of regions with the same size; 2) substituting the voxel model contained in each region into LLE for dimension reduction processing, so as to obtain respiration motion characterization information of the corresponding region; 3) performing Pearson correlation coefficient analysis on the obtained characterization information of each region and the tumor motion information to obtain correlation between the characterization information of each region and tumor motion; and 4) selecting regions with high significance as the effective regions of the body surface, combining the voxel models of the regions, and performing LLE dimension reduction to obtain the body surface motion characterization information.

2.2 Significance Evaluation Function

Figure 3:
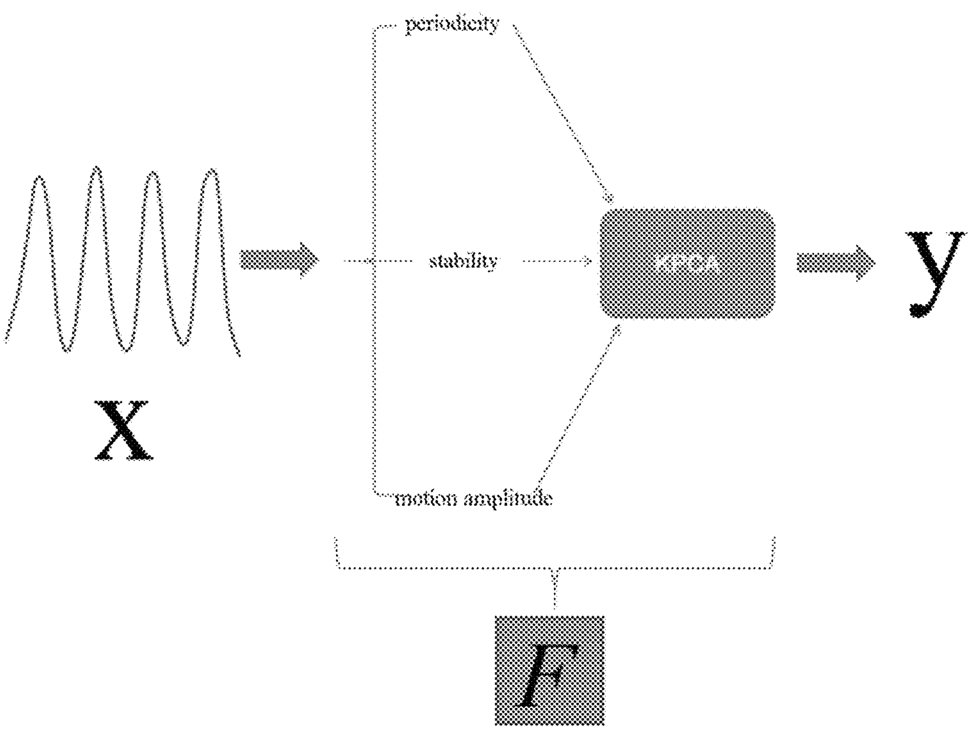
FIG. 3 is a principle diagram of an evaluation function in the present application, in which input x is a region dimension reduction value, F is the evaluation function, and output y is a region significance value.

Although the method described in the above section can obtain distribution of the significant regions, there exists a prerequisite that the tumor motion information is required to be acquired. With the progress of a treatment process, a respiration mode of the patient changes, the corresponding body surface significant region changes correspondingly, and the body surface-tumor association model is required to be updated. However, due to radioactivity of X rays, a pose of a tumor is difficult to acquire in real time. Therefore, the present application proposes an evaluation function for measuring and calculating the significance of the body surface region. The significance of each region can be determined under a condition of unknown tumor motion. By analyzing the body surface respiration feature, three pieces of key characterization information capable of characterizing the significance of different regions of the body surface are extracted: periodicity, stability and motion amplitude of input data, and a dependent variable of the function is a significance value to be solved. If the significance value of a certain region is represented by $\Phi_i$, $\Phi_i$ is solved according to the following formula:

$$\Phi_i = F(\alpha_i, \beta_i, \gamma_i) \tag{1}$$

wherein $\alpha_i$ represents the periodicity, $\beta_i$ represents the stability, $\gamma_i$ represents the motion amplitude, F is an action function, i.e., kernel principal component analysis (KPCA), and the three indexes of the region are subjected to dimension reduction to single values through the KPCA, so as to characterize the significance of the region. An application principle of the evaluation function is shown in FIG. 3, and has a main idea that the final significance value is obtained by dimension reduction of the three index values.

2.2.1 Periodicity Index α

Figure 4:
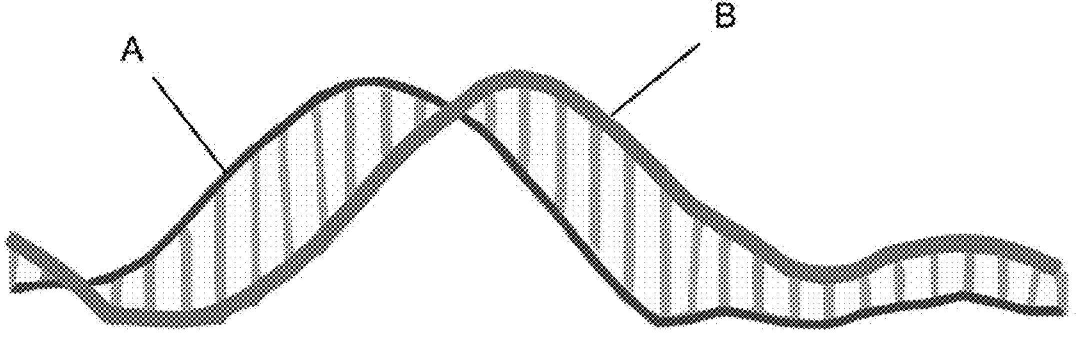
FIG. 4 is a diagram of a corresponding relationship between two groups of data.

Human respiration is rhythmic motion with quasi-periodicity, the body surface motion affected by the respiration motion and in-vivo tumor motion have quasi-periodicity features as well, and therefore, periodicity is selected as an attribute of region data in the present application. The periodicity is generally obtained by solving the correlation between one-dimensional feature data of adjacent periods, and commonly used correlation coefficient solving methods include Pearson, Spearman, Kendall, or the like. However, in the methods, two groups of data with equal lengths are required to be input when the correlation is solved, the quasi-periodic characteristic of human respiration cannot ensure that respiration duration of each period is equal, and corresponding respiration data capacities are different. In order to solve the problem, a dynamic time warping (DTW) algorithm is selected to solve similarity between two groups of adjacent period data in the present application. A length of data is not required to be considered in the DTW algorithm, an end point algorithm is adopted to determine the start and the end of the data, a DTW distance of the two groups of data is calculated to characterize the similarity of the two groups of data, the smaller the distance is, the higher the similarity is, and the larger the distance is, the lower the similarity is. Assuming that the lengths of the two groups of data are n and m respectively, the algorithm first generates two n×m matrices D and d, an element in d is a matching distance of a current frame, and an element in D is an accumulated distance. A solving method of D is as follows:

$$D(i, j) = d(i, j) + \min\begin{cases} D(i-1, j) \\ D(i, j-1) \\ D(i-1, j-1) \end{cases} \tag{2}$$

wherein D(i−1, j), D(i, j−1) and D(i−1, j−1) are accumulated distances of first three points of (i, j). The two groups of data should satisfy the following requirements when generating a corresponding relationship: 1) one-to-one correspondence; 2) unidirectional correspondence; and 3) a minimal distance after correspondence. A schematic diagram of the corresponding relationship of the two groups of data is shown in FIG. 4, the two curves in FIG. 4 represent two groups of data to be matched, curves A and B represent data of two adjacent periods after a body-surface one-dimensional characterization vector division period, sample points contained in the two curves A and B are respiration feature values of the body surface at a current moment, numbers of the sample points are different, but the two curves have certain similarity in shape, and the gray vertical line represents the corresponding relationship between points of the two curves: one-to-one correspondence indicates that each sample point has a corresponding point; unidirectional correspondence indicates that one of the curves A and B serves as an initiator to establish the corresponding relationship (generally, the shorter curve is selected as the initiator), and the other curve serves as a receiver.

The periodicity value of each region is solved, and a process thereof can be divided into the following steps:

1) dividing the region data into a plurality of periods according to the periodicity feature of human respiration motion data;
2) solving the DTW distance between adjacent periods; and
3) summing DTW values and solving an average value, the obtained average value being the periodicity value of the region.

2.2.2 Stability Index β

Due to an influence of the quasi-periodic characteristic of the respiration motion, noise points may appear on data of different regions of the body surface, thus reducing the stability of the data. A number of oscillation points greatly represents the stability of the data, such that the stability of each region is characterized by the number of the oscillation points of the region in the present application. A specific flow is as follows:

1) calculating a number of peak points of dimension reduction data of each region; and
2) to avoid that the selected peak points are true peak-valley points of the data, removing points with a horizontal distance greater than 25 frames (about 1.5s).

2.2.3 Motion Amplitude Index γ

Figure 5:
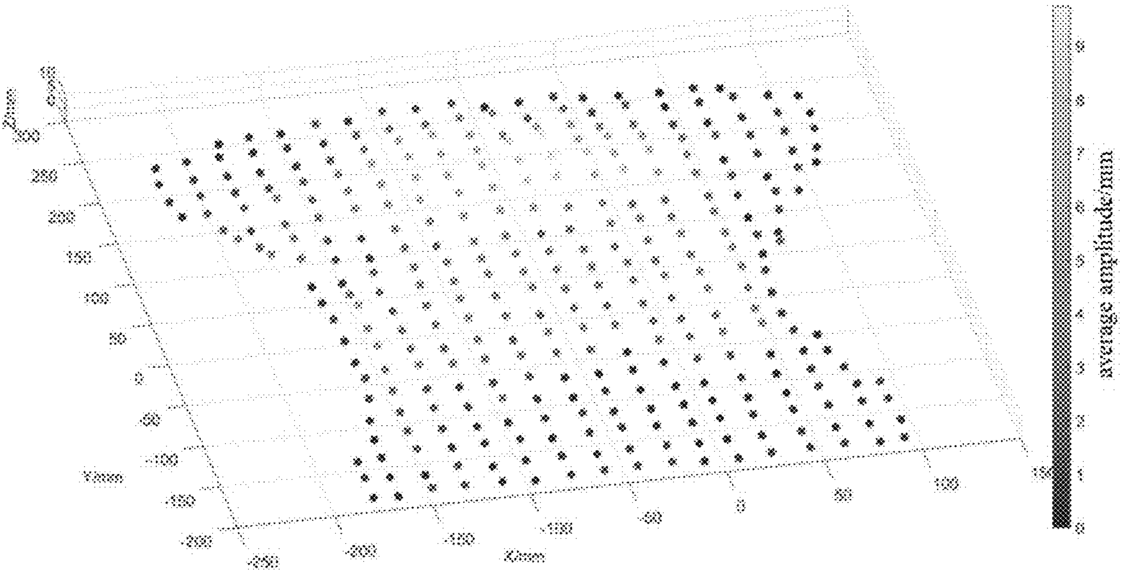
FIG. 5 is a schematic diagram of an average amplitude of a group of point cloud data.

The motion amplitudes of different regions of the body surface of the patient are also different, average amplitude distribution of the point cloud of each region of a respiration motion phantom in 30s is shown in FIG. 5, and the average motion amplitudes of three different regions are shown in table 1.

TABLE 1

Average motion amplitudes of different regions of phantom

| Region | Average motion amplitude (mm) |
|---|---|
| Chest | 6.97 |
| Abdomen | 4.56 |
| Edge | 0.73 |

As can be seen from FIG. 5 and table 1, the high motion amplitude regions of the phantom are mainly concentrated on the chest and abdomen, the amplitudes of the edge regions are small, and the regions with too small motion amplitudes cannot characterize the body surface motion features. Therefore, the motion amplitude is incorporated into the significance index in the present application, and the motion amplitude of the region is obtained by solving a range of the dimension reduction data of the region after smoothing thereof.

2.2.4 Solving of Region Significance

The method for solving the three attribute values of each region of the body surface is introduced above, one-dimensional values capable of characterizing the significance of the region are finally required to be obtained, and therefore, the three attribute values of each region are required to be subjected to dimension reduction to obtain the significance value. The dimension reduction method selected in the present application is KPCA, and different from traditional principal component analysis (PCA), in the KPCA, samples in an input space are mapped to a feature space with higher dimensions or even infinite dimensions by selecting different kernel functions, such that the samples can be linearly divided, and then, PCA dimension reduction is performed on the samples in the feature space. The kernel function selected in the present application is a Gaussian kernel function (RBF), which is widely used due to its higher robustness, and its mathematical form is as follows:

$$K(x_1, x_2) = e^{-\frac{\|x_1 - x_2\|^2}{2\sigma^2}} \quad (3)$$

wherein $x_1$ and $x_2$ are low-dimensional input vectors, and parameter σ controls a range of action of the function.

2.3 Respiration Motion Feature of Effective Region of Body Surface

In the present application, the body surface is uniformly divided into twenty regions (four equal parts in a left-right direction, and five equal parts in an up-down direction), KPCA dimension reduction is performed on the three attribute values of each region to obtain the significance value of the region, high significance regions are selected to be combined into the effective region after the significance values are ranked, and then, LLE dimension reduction is performed on the voxel model of the effective region to obtain the final effective feature of the body surface respiration motion.

3 Experimental Result and Analysis

In this section, comparison experiments are performed on association between respiration motion of marking points of the body surface, overall respiration motion features of the chest and abdomen and the respiration motion features of the effective region and the in-vivo tumor motion, so as to verify a body surface motion information characterization capability of the effective region features. An experimental platform mainly includes: 1) two Kinect v2 depth cameras; 2) a Polhemus Fastrak electromagnetic tracking apparatus; 3) a bionic phantom for chest and abdomen respiration motion; and 4) a POLARIS SPECTRA optical positioning and tracking system apparatus. The depth camera is configured to collect phantom surface motion point cloud information, an electromagnetic tracker is configured to obtain motion information of a tumor on a simulated lung in the phantom, and an NDI apparatus is configured to obtain motion information of three marking points placed on a surface of the phantom. A size of the self-made respiration motion bionic phantom is a size of the upper part of the body of a normal adult male, the surface is made of an elastic silicone material, the phantom is filled with foam particles to support the chest and abdomen surface, a group of hollow simulated lungs are placed at positions corresponding to the lungs of the human body, the simulated lungs realize simulation of the respiration motion by a cylinder system, and work of the cylinder system is converted into a corresponding cylinder volume change quantity by inputting a respiration humidity amount of a real person and respiration speed data, so as to simulate the respiration motion of the real person. Three groups of respiration motion data P1, P2 and P3 of the phantom are collected in the experiment, and each group of data includes body surface point cloud information, marking point data and in-vivo tumor motion information. Before comparison of the experimental results, consistency verification is carried out on the traditional body-surface significant region selection method and the method according to the present application.

3.1 Consistency Verification of KPCA and PCC Methods

The present application provides a method for selecting the significant region of the body surface, including: firstly, solving a Pearson correlation coefficient (PCC) of dimension reduction information of each region and the tumor motion information (referred to as a PCC method below), and taking the coefficient value as a significance characterization quantity of the region, wherein the significance characterization quantity is defined by the following formula:

$$\rho(T, Vi) = \frac{\mathrm{cov}(T, Vi)}{\sigma_T \cdot \sigma_{Vi}} \tag{4}$$

wherein T is the tumor motion information, $V_i$ is the dimension reduction information of the region, and $\sigma_T$ and $\sigma_{Vi}$ are correlation coefficients. After the correlation coefficient of each region is obtained, the regions with high correlation coefficients are selected as the significant regions.

In order to verify whether the significant region selected using the method according to the present application (KPCA method for short) is consistent with the significant region selected using the PCC method, a Bland-Altman analysis method is adopted in the present application. According to the method, an average d of difference values of the results obtained using the two methods and a standard deviation $S_d$ of the difference values are calculated, and a consistency limit interval is defined:

$$[d - 1.96S_d, d + 1.96S_d] \tag{5}$$

Figure 6:
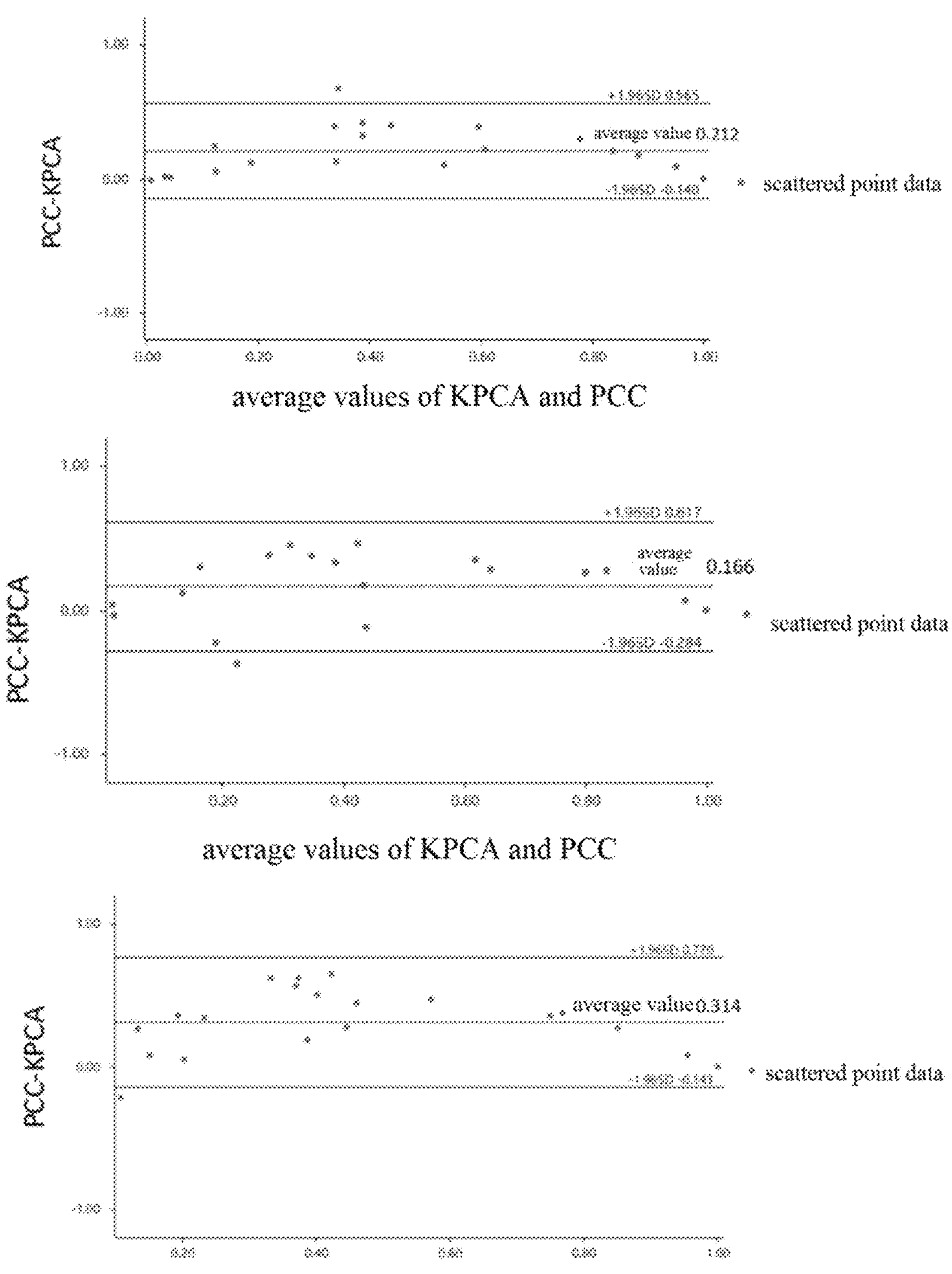
FIG. 6 is a Bland-ALtman diagram of results obtained by KPCA and PCC.

If the difference values of the results obtained using the two methods are mostly in the interval, the two methods are considered to have better consistency; that is, the two methods can be used interchangeably without affecting the quality of the results. The significance values of the feature data of 20 regions of the body surface are solved using the two methods of PCC and KPCA, and normalized, and the results of the Bland-Altman consistency analysis of the significance values of the three groups of phantom data obtained using the two methods of KPCA and PCC are shown in FIG. 6.

Figure 7:
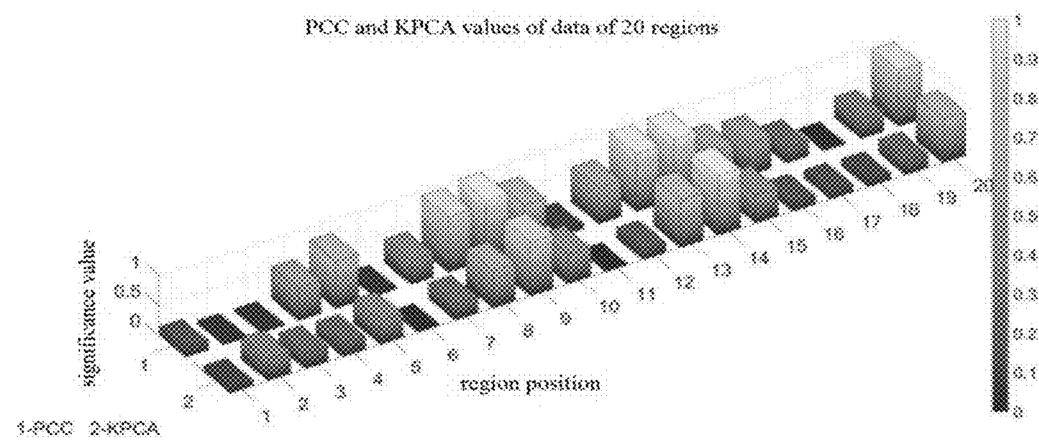
FIG. 7 is a diagram of regional significance results obtained by PCC and KPCA.
Figure 7:
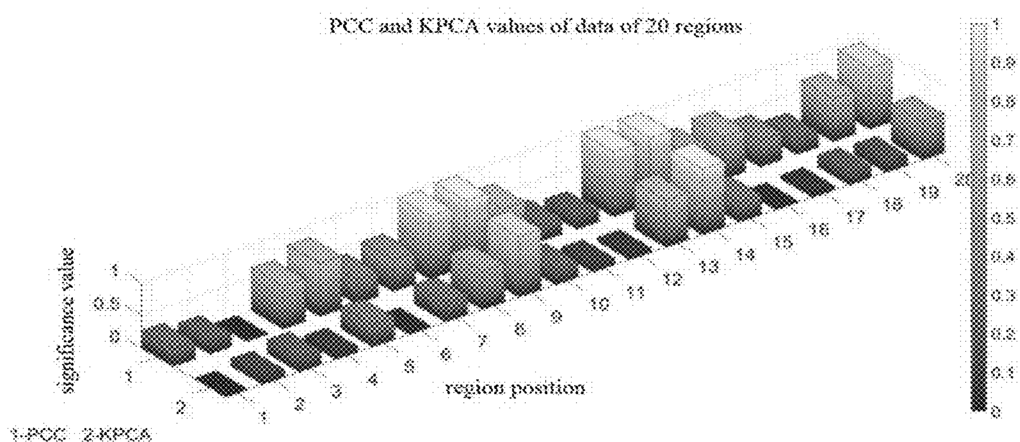
Figure 7:
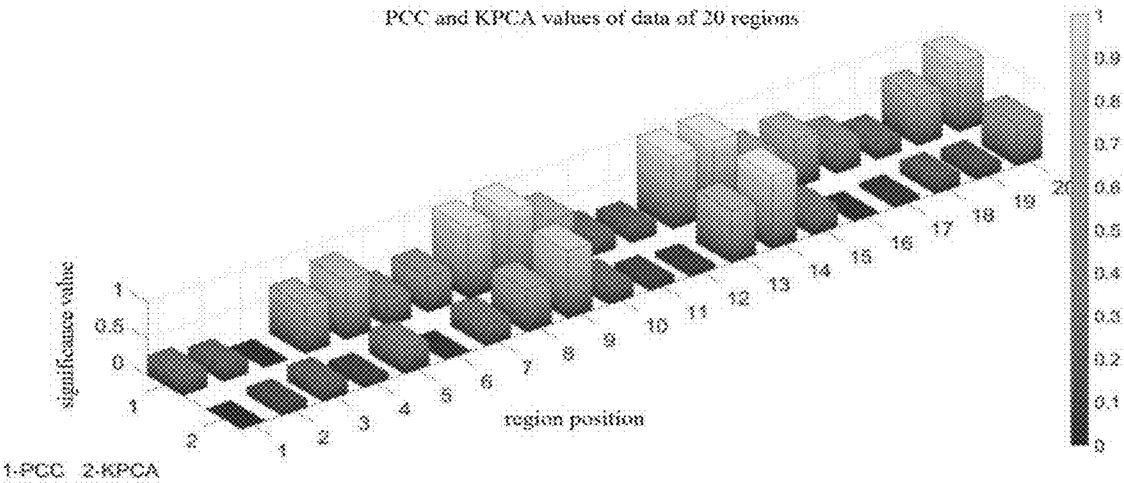

As can be seen from the Bland-Altman diagram, the difference values of the results obtained using the two methods mostly fall within the consistency limit interval, which indicates that the KPCA method and the PCC method have equivalence and can be used interchangeably. For the 20 results obtained using each method, only the regions ranked at the top are taken as the significant regions in the present application, and significance distribution of the regions obtained using the two methods is shown in FIG. 7: as is clear from FIG. 7, the regions with high significance obtained using the two methods are distributed around the 8th, 9th, 13th, 14th, 5th, and 20th regions, and the corresponding body surface is the chest and abdomen region.

3.2 Association Model Error Comparison Experiment

Figure 8:
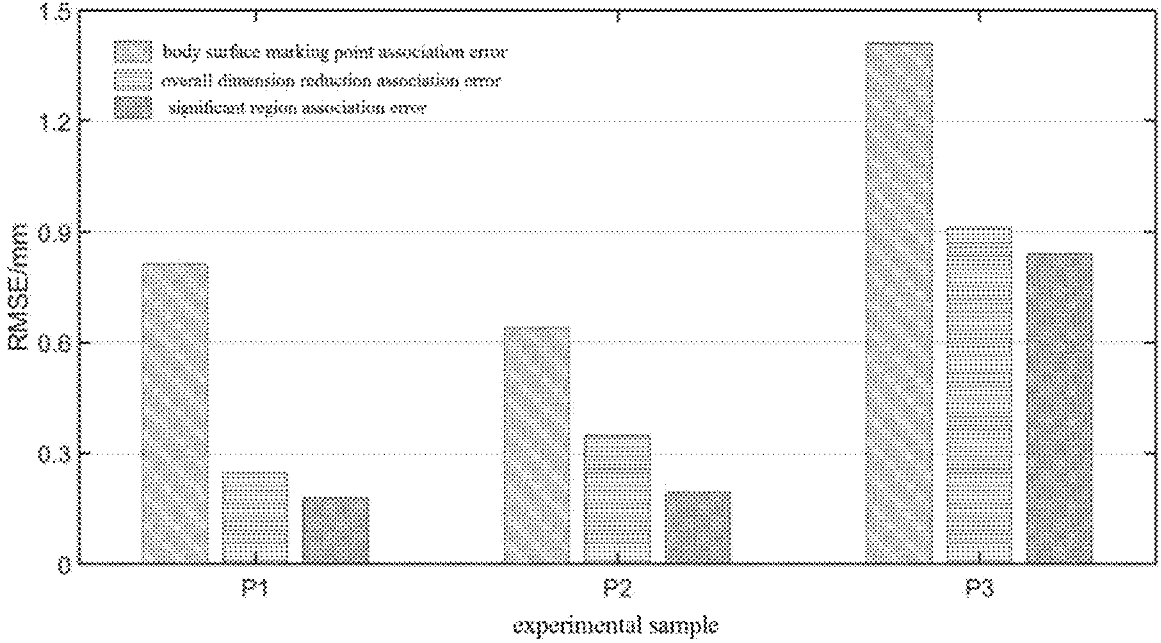
FIG. 8 is a schematic diagram of an association error of three groups of experimental samples.

The three groups of respiration motion data P1, P2 and P3 of the phantom are subjected to respiration time phase division; that is, after the respiration data is divided into an inspiration part and an expiration part, three groups of body surface-in-vivo respiration motion association models are established, and association errors of each group of models are obtained. The models of association between the marking points, the all-body-surface-region dimension reduction information and the effective-region dimension reduction information and the tumor are all polynomial models commonly used in respiration tracking, and an expression thereof is as follows:

$$X_{T_i} = \begin{cases} \sum_{j=0}^{2} A_j^+ x_i^j, & x \geq k_i \\ \sum_{j=0}^{2} A_j^- x_i^j, & x \leq k_i \end{cases} \tag{6}$$

wherein $k_i$ is a boundary point of expiration and inspiration, and $$x_i^j$$

is model input, i.e., the body surface characterization information. $X_{Ti}$ is the tumor motion information, and $$A_j^+$$

and $$A_j^-$$

are polynomial coefficients representing expiration and inspiration phases respectively. A sampling time of samples of each group of experiments is about 35s, and in order to avoid an over-fitting problem of the association model, first 20% of data is selected as a training set, last 80% of the data is selected as a test set, and the association error of each group of experiments is recorded using an output value of the test set. A root mean square error (RMSE) is chosen as a measure of the precision of the association model, and the association errors for three groups of experimental samples are shown in FIG. 8.

The RMSE and a maximum error for each part of data of the three groups of experiments are shown in table 2. In the polynomial model, minimum RMSEs of the marking point data and the all-body-surface-region dimension reduction data are 0.64 mm and 0.25 mm respectively, and a minimum RMSE of the effective-body-surface-region dimension reduction data is 0.18 mm. Comparison of output results of the association models built according to three groups of different body surface characterization quantities is shown in FIG. 9. A tumor motion curve is represented by a solid line, tumor motion values associated with the marking point data are represented by a gray-value medium point curve, and gray-value highest and lowest point curves represent tumor-associated values of the overall dimension reduction data and the effective-region dimension reduction data respectively. The effective-region dimension reduction data represented by the gray-value medium point curve has a better association effect than the gray-value highest and lowest point curves.

TABLE 2

Experimental result error

| | Body surface characterization quantity Association error | Polynomial model RMSE (mm) | Polynomial model MaxErr (mm) |
|---|---|---|---|
| P1 | Marking point data | 0.79 | 2.41 |
| | Overall LLE dimension reduction data | 0.25 | 0.85 |
| | Effective-region LLE dimension reduction data | 0.18 | 0.69 |
| P2 | Marking point data | 0.64 | 1.49 |
| | Overall LLE dimension reduction data | 0.35 | 0.91 |
| | Effective-region LLE dimension reduction data | 0.20 | 0.48 |
| P3 | Marking point data | 1.41 | 4.18 |
| | Overall LLE dimension reduction data | 0.91 | 3.13 |
| | Effective-region LLE dimension reduction data | 0.84 | 2.46 |

With the significance evaluation function provided in the present application, the distribution of the effective regions of the body surface is obtained under the condition of the unknown tumor motion information, the dimension reduction information of the selected effective region has higher precision as the input of the tumor association model, and as can be seen from FIG. 9 and table 2, the association model established according to the respiration motion features obtained by dimension reduction of the chest and abdomen body surface regions selected using the effective region evaluation function has lower RMSE and maximum error.

4 Conclusion

The present application provides the respiration motion characterization method based on a human body chest and abdomen body surface voxel model. Firstly, equal-size region segmentation is performed on the chest and abdomen body surface after three-dimensional reconstruction, significance analysis is then performed on each region of the body surface to obtain the three significance characterization indexes of periodicity, stability and motion amplitude, dimension reduction is performed on the three indexes using KPCA, the significance characterization value of each region is thus calculated, the region with the characterization value ranked at the top is selected as the effective region, and the one-dimensional characterization information is extracted using the LLE dimension reduction algorithm. Finally, the polynomial association model is established for the one-dimensional characterization information after dimension reduction and the in-vivo tumor information. The method can effectively extract the body surface region information with a high characterization capability during the human respiration motion, and compared with the prior art, the method avoids an influence of body-surface redundant motion information on precision of the association model, and compared with the PCC method, the method according to the present application can select the body-surface effective region under the condition of unknown tumor motion information, can realize real-time update of the body-surface effective region during actual radiotherapy, and avoids harm to the human body caused by continuous irradiation of X rays. The body surface motion information can be acquired more accurately by extracting the features of the body-surface effective region, thus facilitating establishment of a more accurate body-surface-in-vivo motion information association model, and providing more accurate treatment precision for a radiotherapy robot. In future research, a more accurate evaluation function is established in conjunction with different respiration modes of the human body to adapt to a condition that the respiration modes change.

What is claimed is:

1. A respiration feature extraction method based on body surface significance analysis, comprising:

establishing a body surface voxel model of chest and abdomen respiration motion, which comprises acquisition of point cloud information, generation of the voxel model and extraction of respiration motion features;

establishing a significance evaluation function by performing significance analysis on different regions of a body surface, and selecting the body surface region with high correlation with tumor motion based on the evaluation function; and performing voxelization on the body surface region, and obtaining effective one-dimensional characterization information of the body surface region using a local linear embedding dimension reduction algorithm, wherein the establishing a significance evaluation function by performing significance analysis on different regions of a body surface, and selecting the body surface region with high correlation with tumor motion based on the evaluation function comprises:

performing equal-size region segmentation on the chest and abdomen body surface after three-dimensional reconstruction;

performing significance analysis on each region of the body surface to obtain three significance characterization indexes of periodicity, stability and motion amplitude;

performing dimension reduction on the three indexes using a kernel principal component analysis algorithm, so as to calculate a significance characterization value of each region; and selecting the region with the characterization value ranked at the top as an effective region.

2. The method according to claim 1, wherein the acquisition of the point cloud information comprises:

unifying coordinates of two Red Green Blue-Depth (RGB-D) depth cameras with fixed positions to the same coordinate system using a calibration plate;

collecting point cloud information of the chest and abdomen body surface by the two RGB-D depth cameras with fixed positions;

removing noise points using a statistical filtering algorithm and registering the two groups of point cloud information using an Iterative Closest Point (ICP) algorithm;

removing redundant information utilizing RGB and boundary threshold segmentation; and smoothing the point cloud data using a mobile least square algorithm.

3. The method according to claim 2, wherein the generation of the voxel model comprises:

inserting the processed point cloud information into Octomap, and creating a voxel map by defining occupied and idle states of the point cloud in a space.

4. The method according to claim 3, wherein the extraction of the respiration motion features comprises:

modeling body surface information of each frame into a voxel model, the voxel model representing a body surface respiration motion state at a moment;

traversing the voxel models of all frames, constructing a rectangular parallelepiped bounding box, i.e., a minimum bounding box, and allowing the bounding box to accommodate the largest one-frame voxel model;

taking out voxel blocks from the bounding box according to the same traversal order for each voxel model, so as to form a one-dimensional column vector; and reducing dimensions of the one-dimensional column vector using a Locally Linear Embedding (LLE) algorithm, so as to obtain a low-dimensional feature capable of characterizing the body surface respiration motion feature.

5. The method according to claim 1, wherein the performing dimension reduction on the three indexes using a kernel principal component analysis algorithm, so as to calculate a significance characterization value of each region comprises:

representing a significance value of a certain region by $\Phi_i$, and then solving $\Phi_i$ according to the following formula:

$$\Phi_i = F(\alpha_i, \beta_i, \gamma_i) \quad (1)$$

wherein $\alpha_i$ represents a periodicity value, $\beta_i$ represents a stability value, $\gamma_i$ represents the motion amplitude, and F is a Kernel Principal Component Analysis (KPCA) action function.

6. The method according to claim 5, wherein a calculation process of the periodicity value comprises:

1) dividing region data into a plurality of periods according to the periodicity feature of human respiration motion data;

2) solving a dynamic time warping (DTW) distance between adjacent periods; and 3) summing DTW values and solving an average value, the obtained average value being the periodicity value of the region.

7. The method according to claim 5, wherein the stability value is characterized by a number of oscillation points of each region, and the process comprises:

1) calculating a number of peak points of dimension reduction data of each region; and 2) removing points with a horizontal distance greater than 25 frames.

8. The method according to claim 5, wherein a calculation process of the motion amplitude comprises:

smoothing the region dimension reduction data, and then solving a range of the region dimension reduction data to obtain the motion amplitude of the region.

9. The method according to claim 1, further comprising:

establishing a polynomial association model for the effective one-dimensional characterization information after dimension reduction and in-vivo tumor information.

* * * * *